United States Patent
Markman

[11] Patent Number: 5,951,572
[45] Date of Patent: Sep. 14, 1999

[54] METHOD, APPARATUS AND KIT FOR PERFORMING HAIR GRAFTS

[76] Inventor: Barry S. Markman, 5157 Jarom, Las Vegas, Nev. 89120

[21] Appl. No.: 09/061,672

[22] Filed: Apr. 16, 1998

Related U.S. Application Data

[63] Continuation-in-part of application No. 08/873,852, Jun. 14, 1997, Pat. No. 5,868,758, which is a continuation-in-part of application No. 08/561,018, Nov. 21, 1995, abandoned, which is a continuation-in-part of application No. 08/395,455, Feb. 28, 1995, Pat. No. 5,643,308.

[51] Int. Cl.$^6$ ..................................................... A61B 17/34
[52] U.S. Cl. ............................................. 606/133; 606/187
[58] Field of Search ............................... 606/1, 131–133, 606/183, 187; 623/15; 604/57, 59–64, 164, 173, 117, 264

[56] References Cited

U.S. PATENT DOCUMENTS

| | | |
|---|---|---|
| 1,061,005 | 5/1913 | Parsegan . |
| 1,694,246 | 12/1928 | Boyne . |
| 3,867,942 | 2/1975 | Bellantoni et al. . |
| 3,945,117 | 3/1976 | Beaver . |
| 3,977,335 | 8/1976 | Bonham . |
| 4,004,592 | 1/1977 | Yamada . |
| 4,126,124 | 11/1978 | Miller . |
| 4,144,876 | 3/1979 | DeLeo . |
| 4,160,453 | 7/1979 | Miller . |
| 4,210,145 | 7/1980 | Nestor et al. . |
| 4,378,019 | 3/1983 | Yamada . |
| 4,451,254 | 5/1984 | Dinius et al. . |
| 4,751,927 | 6/1988 | Yamada . |
| 4,969,903 | 11/1990 | Valle . |
| 5,330,530 | 7/1994 | Hastings . |
| 5,331,472 | 7/1994 | Rassman . |
| 5,360,447 | 11/1994 | Koop . |
| 5,395,368 | 3/1995 | Ellman et al. . |
| 5,439,475 | 8/1995 | Bennett . |
| 5,441,540 | 8/1995 | Kim . |
| 5,490,850 | 2/1996 | Ellman et al. . |
| 5,562,613 | 10/1996 | Kaldany . |
| 5,578,054 | 11/1996 | Arnold . |
| 5,611,810 | 3/1997 | Arnold et al. . |
| 5,611,811 | 3/1997 | Goldberg . |

FOREIGN PATENT DOCUMENTS

| | | |
|---|---|---|
| 96/06566 | 3/1996 | European Pat. Off. . |
| 714642 | 6/1996 | European Pat. Off. . |
| 94/07433 | 4/1994 | WIPO . |
| 95/08947 | 4/1995 | WIPO . |

*Primary Examiner*—Michael Buiz
*Assistant Examiner*—William W. Lewis
*Attorney, Agent, or Firm*—Milbank, Tweed, Hadley & McCloy LLP

[57] ABSTRACT

A device and method are set forth for performing hair grafts which includes a housing, plunger with a needle, and a carriage containing an inventory of hair grafts to be placed. The plunger is placed at an extended position where the needle extends from the catheter and the needle and catheter are inserted into the tissue. The plunger and needle are withdrawn and the carriage is indexed to position a graft. The plunger is moved to urge the graft from the carriage through the catheter into the tissue for transplantation.

17 Claims, 5 Drawing Sheets

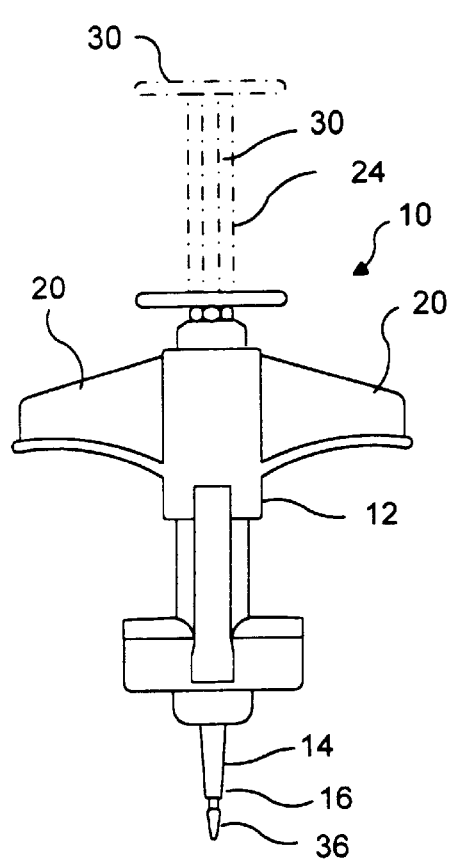
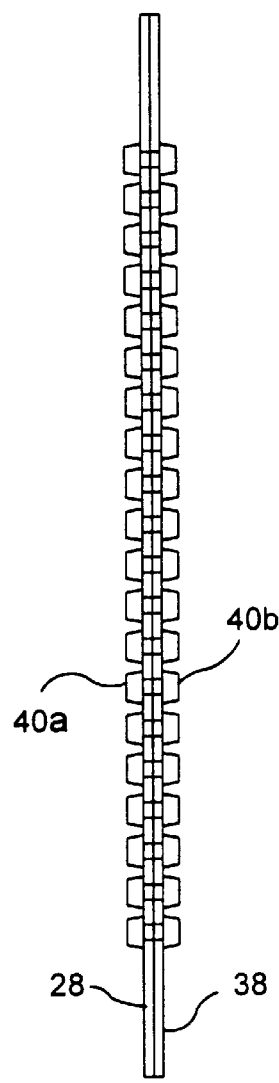
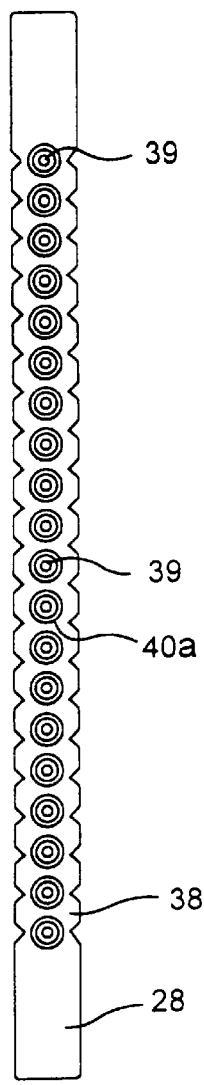
FIG. 1    FIG. 2A    FIG. 2B
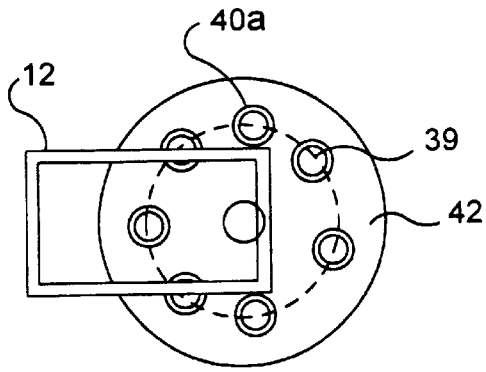
FIG. 3

METHOD, APPARATUS AND KIT FOR PERFORMING HAIR GRAFTS

RELATED APPLICATION DATA

This application is a continuation-in-part of U.S. patent application Ser. No. 08/873,852 filed Jun. 14, 1997, now U.S. Pat. No. 5,868,758, which is a continuation-in-part application of U.S. patent application Ser. No. 08/561,018, filed Nov. 21, 1995, now abandoned, which was a continuation in part of application Ser. No. 08/395,455 filed Feb. 28, 1995, now U.S. Pat. No. 5,643,308.

FIELD OF THE INVENTION

The present invention relates to the placement of hair grafts. In particular, the invention is a device and method for preforming hair grafts.

BACKGROUND OF THE INVENTION

Hair transplants have become commonplace over the last few years. In one of the newest technique of transplanting hair, small "grafts" of tissue containing only a few hairs are placed in sites on a recipient's scalp.

In particular, hair from other portions of the recipient are cut into very small cylindrical sections, or grafts. The recipients scalp is anesthetized, and then expanded by infusing saline into the scalp beneath the galeal layer. The surgeon inserts a needle-like dilator through the scalp, including the galeal layer, forming a cavity. The dilator is removed, and a donor graft is inserted into the cavity.

The success rate of this technique depends primarily upon whether the dilator succeeds in forming a cavity which extends below the galeal layer, and upon the time lapse between preparation and insertion of the graft.

New techniques in hair grafting require a large number, often 200 to 600, grafts to be placed during a single session. In the present technique, dilators are individually placed by hand. This is not only time consuming, but is inexact, since the surgeon places the dilators essentially randomly.

In order for the transplanted hair have a uniform look and proper coverage, however, the grafts must be arranged on the scalp in specific patterns. For example, numerous small grafts are often placed near the hairline, while larger grafts are placed less densely on the top and rear of the scalp.

A need exists for a device and method for easily forming incisions into and dilating the tissue and inserting hair grafts.

SUMMARY OF THE INVENTION

The present invention is directed to a device and method for incising the skin, dilating the tissue and inserting and placing grafts into the incisions.

In the preferred embodiment the device includes a housing having at least one hollow catheter having a diameter adapted to pass a hair graft therethrough. A plunger is moveably disposed on the housing and has a needle with an incising tip adapted to be received into the catheter to move therethrough. The plunger is moveable between a withdrawn position where the needle is withdrawn from the catheter and an extended position where the needle is inserted into the catheter to extend the incising tip therefrom for fashioning an incision in the tissue for insertion of the catheter therein. A cartridge has a plurality of openings each adapted to pass the needle as the plunger moves from the withdrawn position to the extended position. Each opening is also adapted to retain a hair graft. Means are provided for mounting the cartridge to the housing for positioning the openings to register with the catheter.

In use, the plunger is positioned at the extended position and the needle and catheter are inserted into the tissue incising the same and locating the catheter below the galeal layer. The plunger is withdrawn and the cartridge is positioned to register a graft containing opening with the catheter. The plunger is moved toward the extended position which causes the needle to pass through the opening to displace the graft therefrom through the catheter into the incision graft site. The catheter is then pulled from the tissue leaving the graft in place. At the extended position the device is used to make the next incision, the plunger withdrawn, the cartridge indexed to position another opening containing a graft to register with the catheter, the plunger moved to displace the graft from the cartridge through the catheter into the graft site and the catheter removed from the tissue. The foregoing is repeated to deposit the grafts at the incised and dilated sites.

The device may include a single catheter or multiple catheters which provide for the simultaneous placement of multiple grafts.

The cartridge may be in the form of a strip with a plurality of openings each adapted to contain a graft. In an alternative embodiment the cartridge may be in the form of a rotatable disk having a plurality of circumferentially aligned openings each adapted to retain a graft. Means may be provided for indexing the cartridge to serially locate a graft containing opening to register with the catheter(s) in response to movement of the plunger.

In simultaneous multiple site grafting version, the device for creating apertures in the tissue and placing the hair grafts includes a catheter plate having a base with a number of downwardly extending hollow catheters aligned with bores in the base. An incision needle plate comprises a base having a number of downwardly extending needles for extension into the catheters of the incision catheter plate, each needle having at its end an incising tip.

The cartridge plate is provided with sets of openings which are adapted to register with the catheters.

Posts extend upwardly from the incision catheter plate for engagement with bores in each of the other plates for aligned stacking of the plates.

In use, the user presses the incision needle plate and incision catheter plate together until the needle tips extend just beyond the open end of the catheters. The user presses the plates downwardly so that the needle/catheters incise and dilate the tissue of a patient. The user withdraws the incision needle plate, leaving the catheters of the incision catheter plate located in the tissue.

The user locates the hair graft catheter plate (with hair grafts loaded into each catheter) to register the openings with the catheters. The user then presses the hair graft needle plate downwardly so that the needles thereof extend through the hair graft catheter plate, moving the hair grafts downwardly through the catheters to simultaneously deposit them in the tissue. The user then removes all of the plates, leaving the hair grafts in the tissue of the patient.

The user may preload large numbers of hair grafts into the cartridge(s), thereby allowing him to place large numbers of grafts in uninterrupted fashion.

To provide for the location of the catheter dilators by whatever version described above, the present invention includes a method and device for making pre-incisions in the tissue to receive the catheters. The pre-incision device includes a body with a plurality of projecting cutters in a pattern to match the predetermined pattern of the catheters and the desired graft pattern. The surgeon selects the appropriate pattern for the incision device which matches the pattern for the grafts and depresses it to form a pattern of incisions in the tissue to receive the catheters. Pre-incision is useful particularly where simultaneous, multiple grafting is to be used. Because of the distribution of the forces, penetrating the tissue at multiple sites using the catheter/needles may be difficult. By providing the pre-incisions, the catheters can easily be inserted into the pre-made incisions in the tissue.

To guide the use of the incision device, a guide block may be provided. The guide block is adapted to rest on adjacent tissue, i.e. the scalp, to support and guide the movement of the device to make the incision. Guide surfaces can be provided whereby the device may be registered and indexed to make adjacent patterns of incisions.

Further objects, features, and advantages of the present invention over the prior art will become apparent from the detailed description of the drawings which follows, when considered with the attached figures.

BRIEF DESCRIPTION OF THE DRAWINGS

FIG. 1 is a side view of a device according to the present invention for serially transplanting single grafts;

FIGS. 2A–B are respectively side and top views of a cartridge strip for holding a supply of grafts for the device of FIG. 1;

FIG. 3 is a top section view showing the device of FIG. 1 with a cartridge disk for holding a supply of grafts for the device of FIG. 1;

DESCRIPTION

Figure 4:
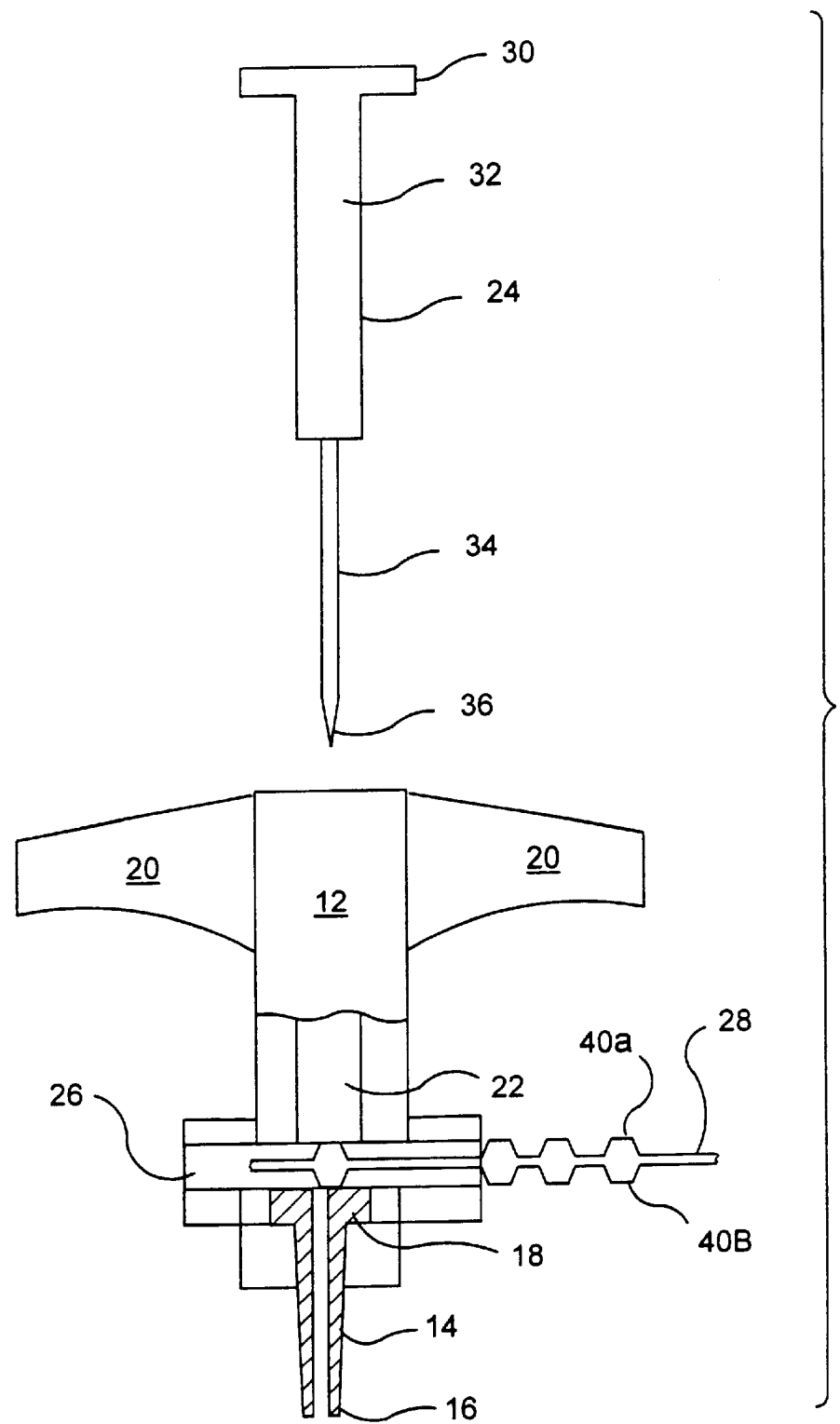
FIG. 4 is an assembly view of the preferred embodiment of the device of FIG. 1.

Turning to FIGS. 1 and 4 a device 10 according to the present invention is shown. The device 10 has a housing 12 mounting at one end a hollow catheter 14 having an outside diameter of approximately 0.085 inches tapering down to approximately 0.065 inches at the end 16 thereof. The catheter 14 is hollow having an inside diameter of approximately 0.048–0.051 inches, a size adapted to pass a hair graft therethrough. The catheter 14 is disposed on a support 18 retained in the housing 12.

Opposite the catheter 14 the housing 12 includes a pair of outwardly projecting handles 20 adapted to provide for stabilization of the device during the incising and transplanting procedure.

A bore 22 extends axially through the housing 12 to receive and guide a plunger 24 for sliding movement therein. The bore 22 may have a diameter of about 0.170 inches. The bore 22 is axially aligned with the axis of the hollow of the catheter 14 and at its terminus intersects a transversely extending passage 26 which, as described below, is adapted to receive, support and guide the movement of a cartridge 28.

The plunger 24 has at one end a head 30 for controlling the movement of the plunger 24 and a barrel 32 adapted to be closely received into the bore 22 of the housing 12. Opposite the head 30 the plunger has a needle 34 of a size to be closely received through the catheter 14 hollow and extend therefrom. At the end the needle 34 has an incising tip 36 which is adapted to incise and puncture tissue.

As suggested in FIG. 1, the plunger 24 is received by the housing 12 for movement between an withdrawn position where the needle 34 is withdrawn from the catheter 14 into the bore 22 and an extended position where the needle 34 passes through the catheter 14 to project the tip 36 from the catheter end 16 for incising the tissue.

The cartridge 28 as shown in FIGS. 2A–B may be embodied as a strip cartridge 28 which has an elongated web 38 having disposed thereon a plurality of openings 39 each adapted to receive an hold a hair graft. To provide for provide for support and retention of the graft each opening 39 has associated therewith axially aligned projections 40a,b extending to either side of the web 38. These projections 40a,b may extend 0.080 inches providing for each opening 39 an axial length of about 0.250 inches to receive and retain the length of a graft. The projections 40a,b may be flared outwardly at each end of the opening 39 to provide a taper to guide insertion of the graft and needle 34 into the opening 39.

Alternatively as shown in FIG. 3, the cartridge 28 may be a disk cartridge 42 having a plurality of the aforesaid openings 39 and projections 40a,b circumferentially aligned thereabout.

Whatever the embodiment the cartridge 28 is adapted to hold an inventory of cultivated grafts for transplantation, the grafts disposed in the openings 39.

As shown in FIG. 4 the cartridge 28 containing the grafts is received into the passage 26 of the housing so as to serially align the openings 39 with the hollow of the catheter 14. As the cartridge 28 is advanced through the passageway 26 hair grafts, as described below, are serially displaced from the openings 39 through the catheter 14 into the tissue for transplantation.

To transplant hair grafts, the grafts are first cultivated and inserted into the openings 39 of the cartridge 28. The cultivation can be done by staff with each graft loaded into on opening 39 of the cartridge. The cartridge 39 is thereafter loaded into the passage 26 of the housing 12 which guides and supports the advancement of the cartridge 39 though the housing 12. The surgeon is now ready to transplant the grafts with the device 10 into the prepared scalp of the patient. By prepared what is meant is that the scalp has been anaesthetized and inflated from the skull with saline solution.

To transplant the grafts with the device 10, the surgeon moves the plunger 24 to the extended position where the needle tip 36 extends from the catheter 14 as shown in FIG. 1. At the location determined by the surgeon, the device 10 is pressed such that the needle 34/catheter 14 combination penetrates the scalp defining an incision. As incised the catheter 14 dilates the tissue of the scalp to receive the graft. With the catheter 14 remaining in and dilating the tissue the plunger 24 is pulled from the housing 12 to the withdrawn position which withdraws the needle 34 from the catheter 14 to a position above, with reference to FIG. 1, the passage 26. The cartridge 28 is advanced through the housing passage 26 to position an opening 39 containing a graft to register with the catheter 14. The plunger 24 is depressed toward the extended position moving the needle 34 through the opening 39 to displace the graft therefrom and push it through the catheter 14 into the dilated incision. The device 10 is withdrawn from the tissue which withdraws the catheter 14 leaving the tissue to close upon the transplanted graft.

The surgeon then repeats the above process at a new site, advancing the cartridge 28 to serially locate openings 39 and the grafts contained therein for transplantation. When the cartridge 39 has been fully advanced through the housing and the grafts retained thereby transplanted, it is discarded and a new, a graft-filled cartridge 28 is inserted and advanced in the manned described above.

Where the cartridge is a disk 42, rather than advancing the cartridge it is rotated to serially advance a graft-retaining opening 39 to register with the catheter 14 where the graft can be moved by the plunger needle 34 through the catheter 14 into the graft site.

Advancement of the cartridge 28 can be by any suitable means such as by hand or by a mechanism which automatically advances the cartridge 28 in response to movement of the plunger 24. Alternatively a separate advancement mechanism such as a rotatable wheel or dial operatively coupled to the cartridge 28 can be used.

Figure 5:
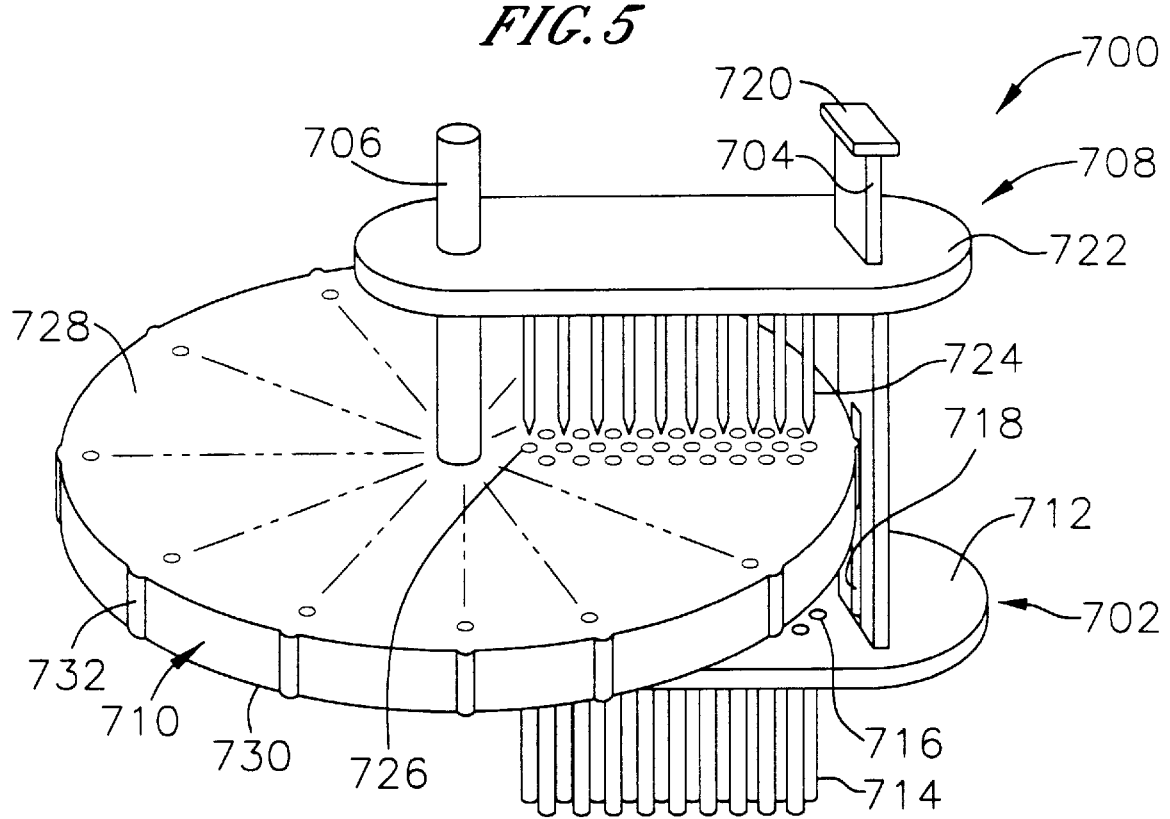
FIG. 5 is a perspective view of a device of a second embodiment of the present invention.
Figure 6:
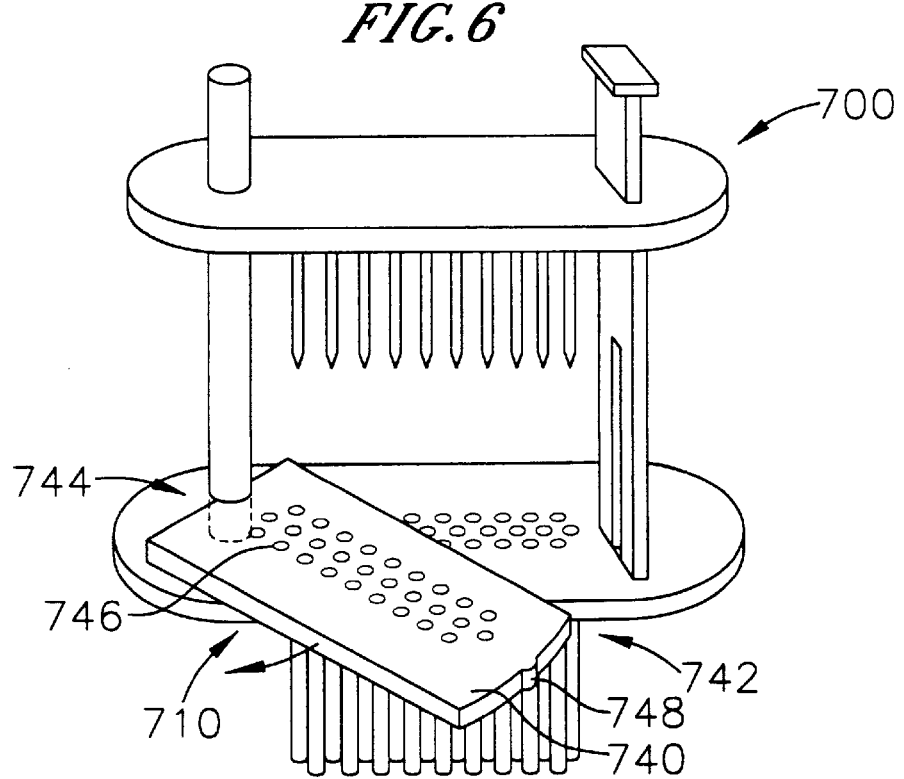
FIG. 6 is a perspective view of another embodiment of the present invention.

Yet another variation of the dilator device for use in the present invention is illustrated in FIGS. 5–6. In this variation of the invention, the templates or plates of the above-described versions of the invention are "mechanized" for faster graft placement.

The device 700 of this form of the invention comprises a first or lower plate 702 having two upwardly extending guides 704,706, an upper or second plate 708 movably mounted on the guides, and a cartridge 710 located between the upper and lower plates.

The lower plate 704 comprises a base member 712 having a number of hollow catheters 714 extending downwardly therefrom and aligned with bores 716 passing through the base. The catheters 714 are arranged on the base 712 in the same pattern in which hair grafts will ultimately be implanted in the tissue of a patient.

The base 712 is preferably fairly rigid and constructed of a durable, sterilizable material, such as plastic. The base 712 is preferably elongate in shape, having first and second ends located outwardly of the bores 716.

Preferably, means for guiding the upper plate 708 between a first raised and a second lowered position are provided. The means preferably comprises guides 704,706 extending upwardly from the ends of the plate 702.

The first guide 704 is a flat member extending upwardly from its connection to the base 712 of the lower plate 702. The guide 704 is fairly wide to accommodate an indentation 718 therein. A stop 720 is located at an end of the guide 704 located opposite the lower plate 702, for limiting the upward movement of the upper plate 708 thereon.

The second guide 706 is a cylindrical post extending upwardly from the end of the base 712 of the lower plate 702 opposite the first guide 704. Both the first and second guides 704,706 are preferably made of a durable and sterilizable material, and have a length sufficient to allow travel of the upper plate 708 between the positions described below.

The upper plate 708 is preferably shaped similar to the lower plate 702, comprising a base 722 having a number of needles 724 extending downwardly therefrom. The needles 724 are cylindrical members having pointed tips which are sized for insertion into the hollow catheters 714 of the lower plate 702 in the manner described above. The length of each needle 724 is chosen such that it extends slightly from the end of the catheter 724 when pressed downwardly therethrough to extend the tip 36 therefrom as described below.

First and second passages are located in the upper plate 708 for acceptance of the first and second guides 704,706, whereby the upper plate 708 may slide up and down along the guides.

As illustrated in FIG. 18, the cartridge 710 comprises a wheel rotatably mounted on the second guide 706 between the lower and upper plates 702,708. The cartridge 710 preferably has a radius equal to the distance between the first and second guides 704,706.

A number of openings 726 pass through the cartridge 710 from a top surface 728 to a bottom surface 730 thereof. The distance between the top and bottom surfaces 728,730 is great enough that a hair graft may be positioned inside each opening 726. Preferably, the openings 726 are arranged in sets about the cartridge. One set is illustrated in FIG. 18. Other sets of openings 726 (not illustrated) are located about the lines illustrated on the top surface 728 of the cartridge 710.

Each set of openings 726 includes a number of openings equal in number to the needles 724 and catheters 714, and arranged in the same pattern.

Means for aligning and registering the sets of openings 726 of the cartridge 710 with the needles 724 and catheters 714 of the plates 702,708 are provided. Preferably, this means comprises a number of beads 732 located on the cartridge 710 and the indentation 718 in the first guide 704.

The beads 732 are located on the outwardly facing surface of the outer edge of the cartridge 710. These beads 732 extend slightly outwardly of the cartridge for engagement with the indentation 718 in the first guide 704. The beads 732 are positioned on the cartridge 710 such that when a bead 732 engages the indentation 718, one of the sets of bores 718 is aligned with the spikes 724 and catheters 714.

Use of this form of the invention is as follows. A user aligns an empty set of openings 726 of the cartridge 710 with the needles 724 and catheters 714. The user accomplishes this by raising the upper plate 708 along the guides 704,706, and then rotating the cartridge 710 until one of the beads 732 engages the indentation 718.

The user then presses the upper plate 706 downwardly, passing the needles 724 through the bores 726 in the cartridge and into the catheters 714. At this time, the tips 36 of the needles 724 protrude slightly from the ends of the catheters 714. The user then presses the device 700 downwardly so that the needles 724 and catheters 714 penetrate and incise the tissue of a patient. The user stops when the lower plate 702 rests on the tissue of the patient.

The user then raises the upper plate 708 until the needles 724 are located above the cartridge 710. The user rotates the cartridge 710 until a set of openings 726 containing hair grafts is aligned with the needles 724. The user or another party can load any of the other sets of openings 726 with hair grafts before or during the procedure. In particular, a user places hair grafts into any or all of the openings 726.

Once aligned, the user presses the upper plate 708 downwardly. As the upper plate 708 moves downwardly, the needles 724 move the hair grafts in the openings 726 down through the catheters 714 into the tissue graft sites. The user then raises the upper plate 708 and removes the device 700 from the tissue. A hair graft is left in the tissue of the patient in each spot corresponding to where a catheter 714 penetrated the tissue and a hair graft was pressed therein.

The user then reinserts the device into the tissue of the patient in a new location and the procedure described above is repeated to transplant another set of grafts.

Advantageously, this device 700 allows a user to pre-load several sets of openings 726 with hair grafts, whereby the device may be used to place several sets of hair grafts in very quick succession.

As illustrated in FIG. 6, a similar result can be achieved when the cartridge 710 used with the device is not a wheel but comprises a single segment. In this version, a cartridge 740 takes the form of a rectangular segment having a first end 742 and a second end 744. Openings 746 like those described above pass through the cartridge 740.

The first end 742 of the cartridge 740 is designed for engagement with the first guide 704. In particular, the first end 742 of the cartridge 740 preferably includes a bead 748 extending outwardly therefrom for engagement with the indentation 718 in the first guide 704.

The second end 744 of the cartridge 740 is designed for engagement with the second guide 706. Preferably, the second end 744 of the cartridge 740 has a semi-circular cut-out.

In use, the user presses the second end 744 of the cartridge 740 into engagement with the second guide 706. The user rotates the cartridge 740 into place when the bead 748 thereon engages the indentation 718 in the first guide 704.

A user utilizes an empty cartridge 740 when inserting the device 700 into the tissue of a patient. The user utilizes a cartridge 740 having openings 746 filled with hair grafts when ready to insert the grafts.

Advantageously, the user may replace cartridges 740 as needed, and when a user has a number of cartridges 740, several may be pre-loaded with hair grafts for quick placement of large numbers of grafts.

According to the forms of the present invention, it is also possible for device to be configured for placement of hair grafts at an angle into the tissue. The catheters, needles and openings may be angled (at other than perpendicular to the plates/cartridge) for placement of the grafts. In that instance, the guides 704,706 should also be angled to permit sliding of the upper plate 708 up and down while the needles move in and out of the openings/catheters.

It has been found that insertion of the dilators defined by the needle/catheter combination according to the above directly into the tissue can be difficult, particularly where a large number of grafts are to be performed. The numerous dilators distribute the force necessary to puncture the tissue making accurate and trouble-free insertion of the dilators difficult. Accordingly, and pursuant to the present invention the device, method and kit are provided.

Figure 7:
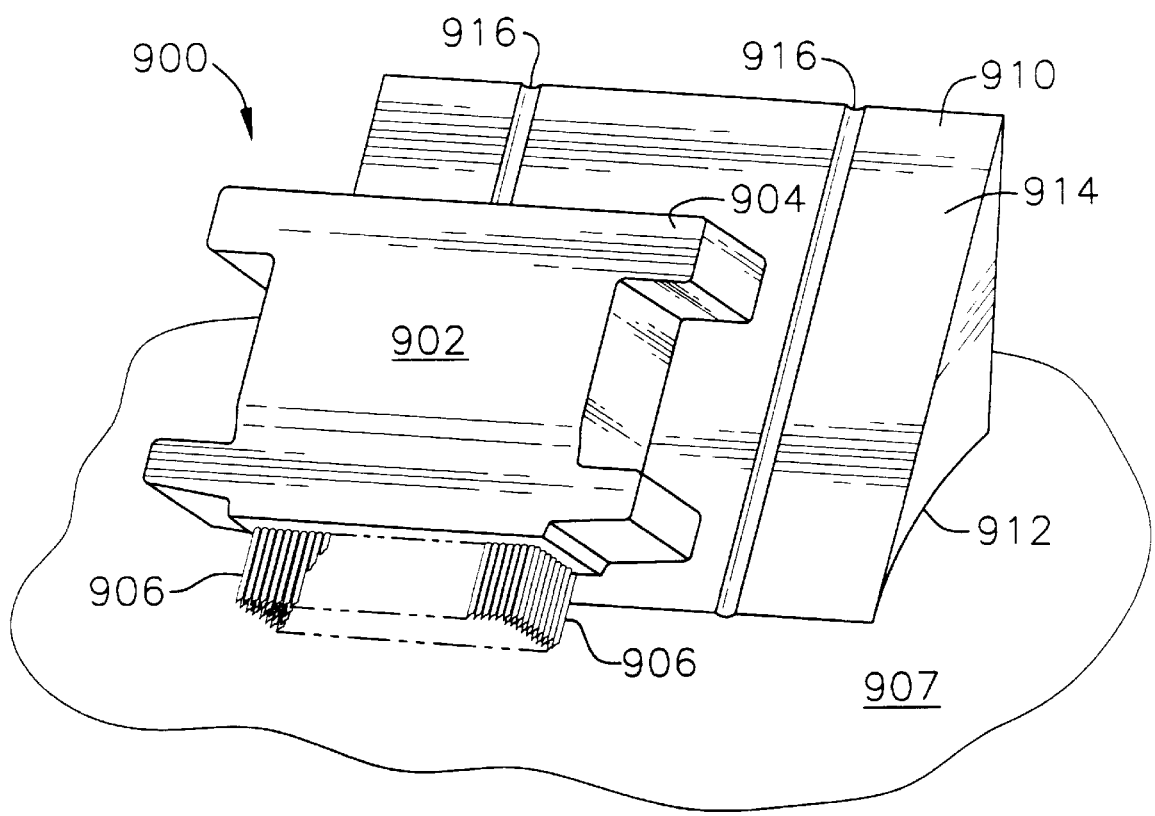
FIG. 7 is a perspective view of the incision device and guide block according to the present invention.
Figure 8:
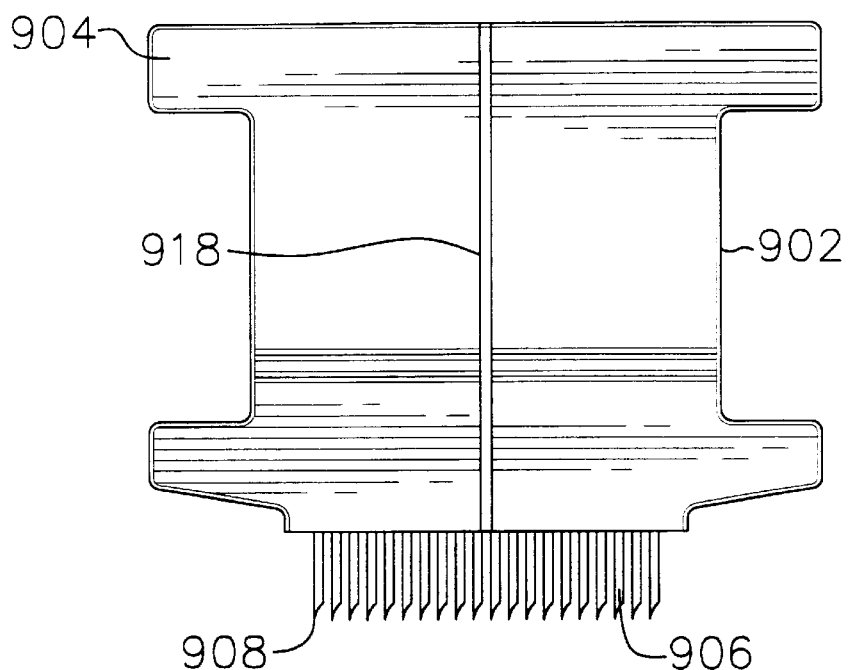
FIG. 8 is a side view of the incision device of FIG. 7.

Turning to FIGS. 7 and 8 an incision device 900 is shown which is adapted to make a pattern of incisions in the tissue to correspond to the pattern of the dilators and grafts to be received therein. The device 900 has a rigid body 902 with at one end a handle 904. Opposite the handle 904 are a plurality of cutters 906, only a portion of the number shown in the drawing, which project from the body 902. These cutters 906 are each adapted to make an incision in the tissue 907 to receive a dilator.

While the cutters 906 may be rigid, solid needles, preferably each is defined as a blade having a tapered knife-edge 908. As shown in FIGS. 21 and 22A–B the cutters 906 are arranged in a pattern which corresponds to the predetermined pattern for the dilators and grafts. It has been found that providing cutters 906 such that each knife-edge 908 makes an incision of about 0.055–0.060 inches deep in the tissue 907 is well suited to receive the dilators.

Figure 9A:
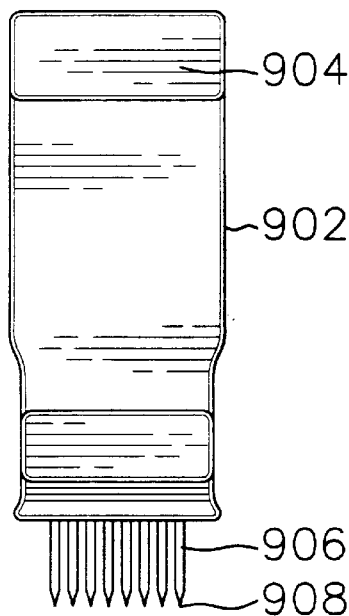
FIGS. 9A–C are views of various embodiments of the incision device of FIG. 7.
Figure 9B:
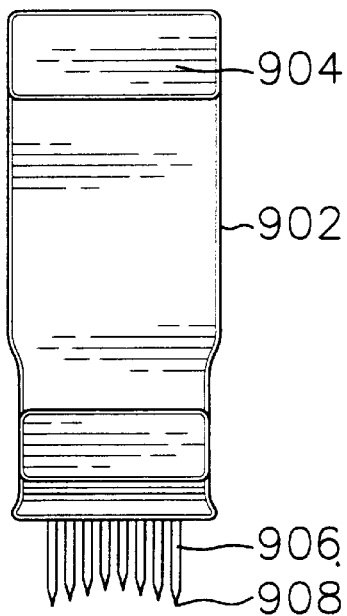
Figure 9C:
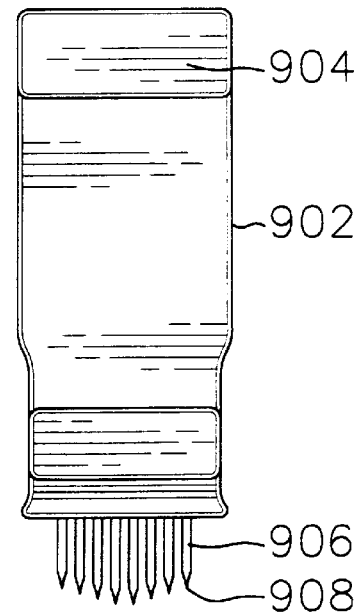

With continuing reference to FIGS. 9A–B the pattern of the cutters 906 can be, as shown in FIG. 9A to make in a single motion an entire row of incisions or can be spaced such that multiple spaced strikes must be made to complete the pattern. That is, the number of cutters would be halved requiring a first strike, indexing over, and a second strike to form the desired pattern of incisions. As shown in FIGS. 9A–C, the cutters 906 of each row are closely spaced to define a minimum spacing for the dilators and grafts. Each row of the pattern formed by the cutters 906 is thus comprised of identical rows and columns of the cutters 906. To facilitate incision and as shown in FIGS. 9B–C, the lengths of the cutters 906 are preferably graduated or staggered so that the entire array of cutters 906 do not penetrate the tissue 907 simultaneously and thereby disadvantageously distribute the penetration forces among all the cutters 906. That is, when the incision device 900 is pressed against the tissue, only a portion of the cutters 906, i.e. one or several columns of the cutter array, are penetrating the outer surface of the tissue 907. Furthermore, the surgeon can rock the device 900 back and forth to make the aforesaid incision pattern defined by the cutter array.

With reference to FIG. 7 the device and method of the present invention may include a guide block 910. The guide block 910 includes a base 912 configured and adapted to rest and support the block 910 on the tissue 907 adjacent the area to be incised. To guide the motion of the incision device 900 the guide block 910 has a guide surface 914 which may be vertical or inclined as shown in the drawings. As shown, the guide surface 914 acts to guide the incision device 900 in its movement toward the tissue 907 to enable the surgeon to accurately align the device with the location on the tissue to be incised.

With continue reference to FIGS. 7 and 8, the guide surface 914 may include a plurality of grooves 916 at spaced locations thereon. To cooperate with the grooves 916 the incision device body 902 includes a rudder 918 projecting therefrom which is sized to be closely received in each groove 916. By engaging the rudder 918 in a groove 916 the movement of the device 900 to the tissue 907 can be easily guided and steadied. Further, where side-by-side incision patterns are to made in the tissue 907, the grooves 916 and rudder 918 act to index the placement of the incisions. A first set of incisions are made and the surgeon indexes the device 900 over to register the rudder into the adjacent groove 916 to make the next pattern of incisions, By sizing the pattern of the cutters 906 and the location of the grooves 916, a consistent larger pattern of incisions can be made in the tissue 907 to receive the grafts.

To make the incision pattern, the surgeon moves the incision device 900 along the guide surface 914 until the cutters 906 engage the tissue 907. The surgeon thereafter stands the device 900 upright and presses down to make the pattern of incisions, If necessary, the surgeon may rock the device from side-to-side to urge the cutters 906 to make the incisions, Once the incisions are made the device 900 is removed from the tissue 907.

Because the incisions are made with the cutters 906, the openings for the grafts are smooth and precise and are made with reduced trauma to the tissue. This, it is believed, will promote healing and acceptance of the graft as well as reduce infection.

After the incisions have been made, the dilators as described above are inserted into the incisions. Since the incision pattern is selected to match the dilator and graft pattern, multiple dilators can be simultaneously inserted into the tissue.

The incision device 900 and the dilator device as well as the guide block may be cooperatively adapted to be sold as a kit. The pattern of cutters 906 and dilators (if the simultaneous, multiple transplantation device of FIG. 5 or 6 is selected) would correspond to a selected pattern for the grafts. The graft pattern may vary depending upon the desired density of the grafts to be implanted.

It will be understood that the above described arrangements of apparatus and the method therefrom are merely illustrative of applications of the principles of this invention and many other embodiments and modifications may be made without departing from the spirit and scope of the invention as defined in the claims.

I claim:

1. A device for serially transplanting hair grafts comprising;

a housing supporting a hollow catheter;

a plunger moveably disposed on the housing and having a needle with an incising tip adapted to be received into the hollow of the catheter to move therethrough, said plunger moveable between a withdrawn position whereat the needle is withdrawn from the catheter and an extended position whereat the needle tip extends from the catheter for fashioning an incision to receive a graft therein;

a cartridge including a plurality of openings each adapted to pass said needle as the plunger moves from the withdrawn to the extended position and to retain a graft to be transplanted; and said cartridge mounted to the housing for positioning the openings to align with the catheter for displacement of the graft by the needle from the cartridge through the catheter into the incision as the plunger is moved between the withdrawn to the extended position.

2. The device of claim 1 wherein the cartridge defines a strip having said openings along its length.

3. The device of claim 1 wherein the cartridge is a circular disk having said openings about its circumference.

4. The device of claim 1 wherein said cartridge is indexable to serially align the openings with the catheter.

5. The device of claim 3 wherein said cartridge includes circumferentially aligned projections including an axial throughbore to define each of said openings.

6. A device for serially transplanting hair grafts into incisions made in the skin comprising;

a housing supporting a hollow catheter;

a plunger moveably disposed on the housing and having a spike having an incising tip adapted to be received into the hollow of the catheter to move therethrough, said plunger moveable between a withdrawn position whereat the spike is withdrawn from the catheter and an extended position whereat the spike extends from the catheter for fashioning an incision to receive a graft therein;

a cartridge strip including aligned therealong a plurality of openings each adapted to pass said spike as the plunger moves from the withdrawn to the extended position and to retain a graft to be transplanted; and said cartridge strip mounted to the housing for serially positioning the openings to a drive position whereat an opening containing a graft is aligned with the catheter for displacement of the graft by the spike from the cartridge strip through the catheter into the incision as the plunger is moved between the withdrawn to the extended position.

7. The device of claim 6 wherein said cartridge strip is indexable to serially position said openings to said drive positions.

8. A device for serially transplanting hair grafts into incisions made in the skin comprising;

a housing supporting a hollow catheter;

a plunger moveably disposed on the housing and having a spike adapted to be received into the hollow of the catheter to move therethrough, said plunger moveable between a withdrawn position whereat the spike is withdrawn from the catheter and an extended position whereat the spike extends from the catheter for incising and dilating the skin to receive a graft;

a cartridge disk including aligned circumferentially therealong a plurality of openings each adapted to pass said spike as the plunger moves from the withdrawn to the extended position and to retain a graft to be transplanted; and said cartridge disk mounted to the housing for serially positioning the openings to a drive position whereat an opening containing a graft is aligned with the catheter for displacement of the graft by the spike from the cartridge disk through the catheter into the incision as the plunger is moved between the withdrawn to the extended position.

9. The device of claim 8 wherein said cartridge disk is indexable to serially position said openings to said drive positions.

10. A method for placing hair grafts in an incision in the skin comprising;

providing a device including a housing having a hollow sleeve, a plunger having a pin adapted to be received into the hollow of the sleeve and moveable disposed on the housing for movement between a withdrawn position and an extended position and a cartridge having a plurality of openings each adapted to register with the sleeve and to retain a graft;

locating the sleeve in an incision;

moving the plunger from the withdrawn position toward the extended position for the pin to urge a graft from an opening through the sleeve into the incision for implantation thereof;

withdrawing the plunger to remove the pin from the sleeve; and repositioning the cartridge to register another opening containing a graft with the sleeve.

11. The method of claim 10 including repositioning the cartridge in response to movement of the plunger.

12. A device for serially transplanting hair grafts into tissue which has been incised and dilated comprising;

a housing;

a cartridge disposed on the housing and having a plurality of openings each adapted to retain a graft for transplantation thereof;

said cartridge indexable to serially align openings to a delivery position; and means for moving the graft from said cartridge opening at the delivery position into the tissue for transplantation thereof.

13. The device of claim 12 wherein the cartridge is a strip having a plurality of said openings along the length thereof.

14. The device of claim 12 wherein the cartridge is a disk having said openings disposed in a circular pattern and said cartridge is indexably rotatable to serially align said openings to said delivery position.

15. The device of claim 12 wherein said graft moving means includes a plunger moveably disposed on the housing and having a needle adapted to be received into the hollow of a catheter to move there through, said plunger moveable between a withdrawn position whereat the needle is withdrawn from the catheter to an extended position to extend through the opening aligned at the delivery position to move a graft therefrom through the catheter into the dilated incision.

16. A device for serially transplanting hair grafts into tissue which has been incised and dilated comprising:

a housing;

a cartridge strip disposed on the housing and having a plurality of openings along the length thereof each adapted to retain a graft for transplantation thereof;

said cartridge strip indexable to serially align openings to a delivery position; and means for moving the graft from cartridge opening at the delivery position into the tissue for transplantation thereof.

17. A device for serially transplanting hair grafts into tissue which has been incised and dilated comprising:

a housing;

a cartridge disk disposed on the housing and having a plurality of openings disposed in a circular pattern each adapted to retain a graft for transplantation thereof;

said cartridge disk indexable to serially align openings to a delivery position; and means for moving the graft from cartridge opening at the delivery position into the tissue for transplantation thereof.

* * * * *

UNITED STATES PATENT AND TRADEMARK OFFICE
CERTIFICATE OF CORRECTION

PATENT NO. : 5,951,572
DATED : September 14, 1999
INVENTOR(S) : Barry S. Markman It is certified that error appears in the above-identified patent and that said Letters Patent is hereby corrected as shown below:

Title page, Related U.S. Application Data, item [63], third line, "application No. 08/561,018, November 21, 1995, abandoned," should read -- application No. 08/561,018, November 21, 1995, Pat. No. 5,792,169, --.

Column 1, lines 8-9, "U.S. patent application Ser. No. 08/561,018, filed November 21, 1995, now abandoned" should read -- U.S. Patent application Ser. No. 08/561,018, filed Nov. 21, 1995, now U.S. Pat. 5,792,169 --.

Signed and Sealed this

Twentieth Day of February, 2001

Attest:

NICHOLAS P. GODICI

Attesting Officer     Acting Director of the United States Patent and Trademark Office